United States Patent
Mukkamala et al.

(10) Patent No.: US 10,136,823 B2
(45) Date of Patent: Nov. 27, 2018

(54) METHODS AND APPARATUS FOR DETERMINING CUFF BLOOD PRESSURE

(71) Applicant: Board of Trustees of Michigan State University, East Lansing, MI (US)

(72) Inventors: Ramakrishna Mukkamala, Okemos, MI (US); Jiankun Liu, Lansing, MI (US); Jin-Oh Hahn, College Park, MD (US)

(73) Assignee: Board of Trustees of Michigan State University, East Lansing, MI (US)

( * ) Notice: Subject to any disclaimer, the term of this patent is extended or adjusted under 35 U.S.C. 154(b) by 594 days.

(21) Appl. No.: 14/012,124

(22) Filed: Aug. 28, 2013

(65) Prior Publication Data

US 2014/0066793 A1 Mar. 6, 2014

Related U.S. Application Data

(60) Provisional application No. 61/693,812, filed on Aug. 28, 2012.

(51) Int. Cl.
*A61B 5/02* (2006.01)
*A61B 5/022* (2006.01)
*A61B 5/0225* (2006.01)

(52) U.S. Cl.
CPC ............ *A61B 5/02225* (2013.01); *A61B 5/02* (2013.01); *A61B 5/02208* (2013.01); *A61B 5/02241* (2013.01); *A61B 5/02255* (2013.01)

(58) Field of Classification Search
CPC .... A61B 5/02; A61B 5/02208; A61B 5/02225
See application file for complete search history.

(56) References Cited

U.S. PATENT DOCUMENTS

| | | | |
|---|---|---|---|
| 5,423,322 A | 6/1995 | Clark et al. |
| 5,590,662 A | 1/1997 | Hersh et al. |
| 6,458,085 B1 | 10/2002 | Wu et al. |
| 6,733,461 B2 | 5/2004 | Bratteli |
| 6,767,328 B2 | 7/2004 | Kulik |
| 6,808,496 B2 | 10/2004 | Oka et al. |
| 6,893,403 B2 | 5/2005 | Kolluri et al. |
| 7,186,218 B2 | 3/2007 | Hersh et al. |
| 7,288,070 B2 | 10/2007 | Kolluri et al. |
| 7,775,987 B2 | 8/2010 | Hersh et al. |

(Continued)

OTHER PUBLICATIONS

Drzewiecki et al., Theory of the Oscillometric Maximum and the Systolic and Diastolic Detection Ratios, Annals of Biomedical Engineering, vol. 22, pp. 88-96, 1994.*

(Continued)

*Primary Examiner* — Puya Agahi
(74) *Attorney, Agent, or Firm* — Harness, Dickey & Pierce, PLC

(57) ABSTRACT

A method is provided for determining blood pressure for a subject using a sphygmomanometer. The method includes: measuring an oscillometric cuff pressure waveform of the subject using the sphygmomanometer; representing the measured waveform with a physical model accounting for mechanics of the cuff, an artery and coupling between the cuff and the artery; determining the model unknowns from the measured waveform; and determining blood pressure for the subject using the determined model.

6 Claims, 12 Drawing Sheets

(56) References Cited

U.S. PATENT DOCUMENTS

| | | | |
|---|---|---|---|
| 2010/0324384 A1* | 12/2010 | Moon | A61B 5/0245 600/323 |
| 2010/0324429 A1* | 12/2010 | Leschinsky | A61B 5/02208 600/493 |
| 2012/0136605 A1 | 5/2012 | Addison et al. | |
| 2014/0066788 A1 | 3/2014 | Mukkamala et al. | |
| 2014/0066793 A1 | 3/2014 | Mukkamala et al. | |
| 2014/0163402 A1 | 6/2014 | Lamego et al. | |

OTHER PUBLICATIONS

Babbs, Oscillometric measurement of systolic and diastolic blood pressures validated in a physiologic mathematical model, BioMedical Engineering Online 2012, 11:56, pp. 1-22.*

S. Yoon, et al., "Simulation of Estimating the Blood Pressure Using an Arterial Pressure-Volume Model", 2007 International Conference on Convergence Information Technology (ICCIT 2007), pp. 2181-2186 (2007).

T. Kim, et al., "A New Blood Pressure Measurement Using Dual-Cuffs", 2008 Computers in Cardiology, pp. 165-168 (2008).

J. Jilek, et al., "Dual-Cuff System Improves Noninvasive Blood Pressure Determination", Applied Electronics (AE), 2010 International Conference, pp. 2-5 (2010).

M. Forouzanfar, et al., "Mathematical Modeling and Parameter Estimation of Blood Pressure Oscillometric Waveform", 2012 IEEE International Symposium on Medical Measurements and Applications Proceedings, pp. 1-6 (2012).

C. Babbs, "Oscillometric Measurement of Systolic and Diastolic Blood Pressures Validated in a Physiologic Mathematical Model", Biomedical Engineering Online, vol. 11, p. 45 (2012).

M. James "Simplified Model for the Design of an Oscillometric Blood Pressure Measuring System", A thesis presented to the University of Guelph, Guelph, Ontario, CA (2012).

* cited by examiner

METHODS AND APPARATUS FOR DETERMINING CUFF BLOOD PRESSURE

CROSS-REFERENCE TO RELATED APPLICATIONS

This application claims the benefit of U.S. Provisional Application No. 61/693,812, filed on Aug. 28, 2012. The entire disclosure of the above application is incorporated herein by reference.

GOVERNMENT RIGHTS

This invention was made with government support under 0643477 awarded by the National Science Foundation and under W81XWH-11-2-0016 awarded by the U.S. Army. The government has certain rights in the invention.

FIELD

The present disclosure relates to methods and apparatus for determining cuff blood pressure based on a physical model.

BACKGROUND

Blood pressure is the pressure exerted by the blood on the vessel wall. It is a principal vital sign. Various methods, both invasive and non-invasive, have been developed for its measurement.

Invasive methods are employed by penetrating the arterial wall and are typically restricted to critically ill patients. Non-invasive methods are much more common and generally involve the use of an inflatable cuff.

The standard non-invasive method is auscultation. This method measures systolic and diastolic pressures (SP and DP) by occluding a brachial artery with an inflatable cuff and then detecting the Korotkoff sounds during the deflation period with a stethoscope while observing the pressure inside the cuff with a sphygmomanometer. However, this method requires a trained operator to make the measurement.

The most widely used automated and non-invasive method is perhaps oscillometry. This method determines SP, DP, and mean pressure (MP) using an inflatable cuff, which acts as both an external pressure applicator and a blood volume sensor. More specifically, as shown in FIG. 1a, the cuff is likewise placed over usually a brachial artery and inflated to a supra-SP level (e.g., 180 mmHg) and then slowly deflated to a sub-DP level (e.g., 50 mmHg). So, during the deflation period, the brachial artery experiences trans-mural pressures ranging from negative to positive values. Since arterial compliance changes considerably around zero trans-mural pressure, the amplitude of the blood volume oscillation (due to the heart beat) varies greatly. This variation accordingly alters the amplitude of the resulting pressure oscillation that is sensed inside the cuff as illustrated in FIG. 1b. The blood pressure values are then estimated from this oscillometric cuff pressure waveform (i.e., the waveform indicating the time evolution of the pressure inside the cuff during inflation and deflation of the cuff as shown in FIG. 1a).

The original and most popular blood pressure estimation method is as follows. First, the oscillometric cuff pressure waveform is high-pass filtered as shown in FIG. 1b. Then, the envelope of the high-pass filtered waveform is determined as also shown in FIG. 1b. Next, since the arterial compliance becomes maximal when unloaded (i.e., at zero trans-mural pressure), MP is estimated as the cuff pressure at which the envelope is maximal as shown in FIG. 1. SP and DP are then estimated as the cuff pressures at which the amplitude of the envelope is some ratio of its maximum value. The ratios are fixed to empirically selected values (e.g., 0.61 before the envelope maximum occurs for SP and 0.74 after the envelope maximum occurs for DP as shown in FIG. 1) rather than being specific to the patient at the time of measurement. As a result, this "fixed-ratio" method is heuristic and can be very inaccurate. The method may be especially error prone with arterial stiffening (i.e., decrease in arterial compliance around zero trans-mural pressure) and changes in pulse pressure (PP=SP−DP).

Numerous methods have been developed to improve upon the fixed-ratio method. These methods can be categorized into at least four groups.

One group of methods employs more than one cuff. However, these methods are obviously less practical.

A second group of methods seeks to obtain a more accurate or more complete high-pass filtered waveform envelope. However, the fixed-ratio method is then used to determine the BP values.

A third group of methods apply methods different from the fixed-ratio method to estimate the blood pressure values. One method uses the phase spectrum of the oscillometric cuff pressure waveform. This method, by itself, cannot estimate MP. In addition, the method likewise resorts to empirical means to estimate SP and DP from the phase spectrum variations and may therefore yield no improvement in accuracy. Another method analyzes the shape of each beat of the oscillometric cuff pressure waveform. In particular, the duty ratio is calculated as the ratio of the non-flat duration of the beat to the entire duration of the beat. This ratio increases as the pressure applied by the cuff decreases, since trans-mural pressure increases and more oscillatory components can be observed. SP and DP are then estimated from the duty ratio using population statistics. Hence, the method is similarly empirical and may not improve accuracy.

A fourth group of methods estimates the entire blood pressure waveform rather than just DP, MP, and SP. First, DP, MP, and SP are estimated from the oscillometric cuff pressure waveform. Then, the cuff pressure waveform is measured at a constant cuff pressure, which is usually sub-DP (e.g., 60 mmHg). Finally, this waveform is calibrated with the SP, MP, and/or DP to arrive at an estimated blood pressure waveform. However, the waveform that is measured is, in fact, a blood volume waveform. Further, the arterial compliance is nonlinear. Hence, blood volume is, in general, not linearly related to blood pressure.

A more accurate method for automated and non-invasive measurement of the blood pressure waveform is finger-cuff photoplethysmography (PPG). This less popular method employs a finger-cuff with a PPG (which measures a blood volume waveform) embedded in it and the arterial unloading principle. First, the cuff is likewise inflated and deflated while measuring the PPG to yield a finger oscillometric blood volume waveform. Then, the blood volume at which the artery is unloaded is estimated. One possible way is to find the average blood volume at which the amplitude of the oscillometric blood volume waveform envelope is maximal during the deflation period. Finally, the cuff pressure is continuously varied so as to maintain this blood volume throughout the cardiac cycle via a fast, servo-control system. In this way, the cuff pressure equals the pressure inside the artery. Since the unloaded blood volume can change (e.g., due to vasomotor tone), it must be estimated periodically. However, the need for the sophisticated servo-control system makes this method prohibitively expensive. Further, the continual unloading of the artery restricts blood flow to the finger. As a result, subjects often cannot tolerate the method for very long time periods (e.g., at most on the order of hours).

In sum, blood pressure estimation from the oscillometric cuff pressure waveform is empirical and therefore generally error prone, while blood pressure measurement via the arterial unloading principle is expensive and inconvenient. Methods and apparatus are needed to overcome these limitations and thereby improve blood pressure measurement.

This section provides background information related to the present disclosure which is not necessarily prior art.

SUMMARY

This section provides a general summary of the disclosure, and is not a comprehensive disclosure of its full scope or all of its features.

A method is provided for determining blood pressure for a subject. The method includes: measuring the oscillometric cuff pressure waveform from the subject; representing the measured waveform with a physical model; determining the model unknowns using the measured waveform; and determining blood pressure for the subject using the determined model.

One exemplary embodiment is a parametric method. The method includes: measuring the oscillometric cuff pressure waveform from the subject; representing the measured waveform in terms of the unknown parameters of a physical model accounting for the cuff and artery and their coupling; estimating the model parameters from the measured waveform, the known volume of air pumped into and out of the cuff, and a priori measurements on the cuff; and determining blood pressure for the subject using the parameter estimates.

Another exemplary embodiment is a non-parametric method. The method includes: measuring the oscillometric cuff pressure waveform from the subject; representing the measured waveform in terms of a physical model accounting for the cuff and artery and their coupling; determining the blood volume or vessel area waveform based on this model from the measured waveform, the known volume of air pumped into and out of the cuff, and a priori measurements on the cuff; determining non-parametrically the blood volume or vessel area-blood pressure relationship from the determined and measured waveforms; and determining blood pressure for the subject using the determined relationship and determined waveform.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Figure 1A:
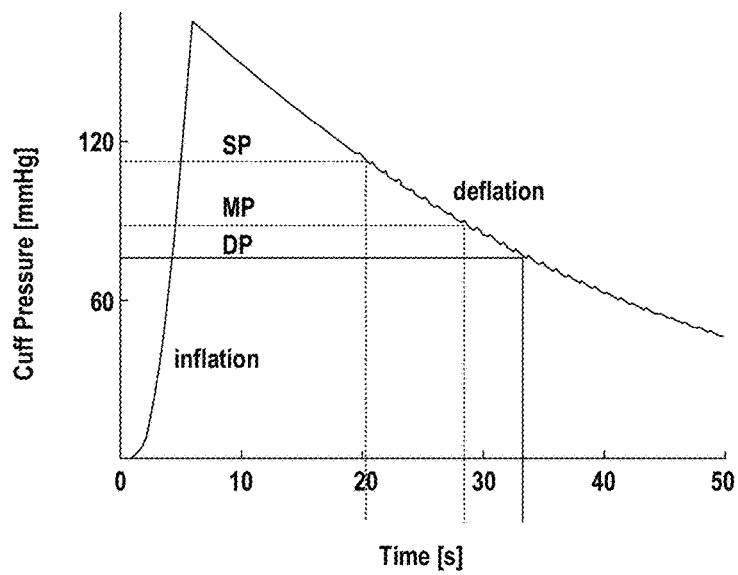
FIGS. 1A and 1B are a graph illustrating the fixed-ratio method for estimating diastolic, mean, and systolic blood pressures (DP, MP, SP) from the oscillometric cuff pressure waveform.
Figure 1B:
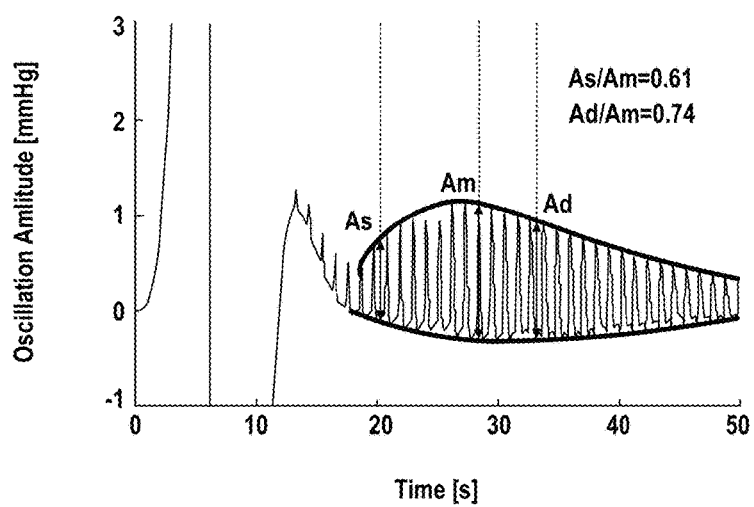
Figure 2:
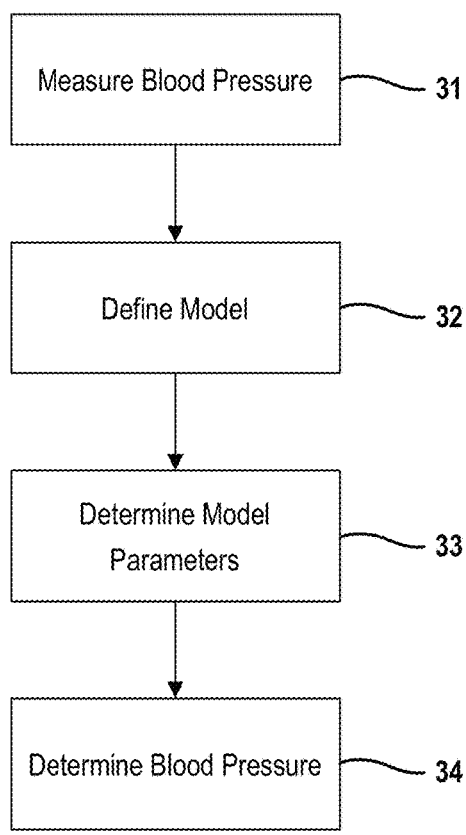
FIG. 2 is a flowchart providing an overview of an example method for determining blood pressure for a subject.

FIG. 2 is a diagram depicting an example method for determining cuff blood pressure. The present disclosure encompasses the recognition that cuff blood pressure measurement may be improved by using a physical model of the underlying phenomena. More specifically, an oscillometric cuff pressure waveform is measured at 31 from a subject with a standard arm cuff. The oscillometric cuff pressure waveform is represented at 32 with a physical model. The model accounts for the mechanics of the cuff and artery and their coupling, which may or may not incorporate the mechanics of the compressible arm tissue. The model unknowns are determined at 33 from the oscillometric cuff pressure waveform. Finally, DP, MP, SP and the blood pressure waveform are determined at 34 using the model. In this way, the estimation of blood pressure is specific to the subject at the time of measurement and therefore more accurate.

Alternatively, an oscillometric blood volume waveform is measured from a subject with a finger-cuff PPG device, and a physical model is used to represent the blood volume-blood pressure relationship. Then, the model is determined from the oscillometric blood volume and cuff pressure waveforms. Finally, the blood pressure waveform is determined using the model. The blood pressure waveform may also be subsequently determined from only the blood volume waveform using the model. In this way, the blood pressure waveform is continuously obtained with a finger-cuff PPG device without the need for invoking the expensive and inconvenient arterial unloading principle.

In either case, the determined blood pressure waveform may be mathematically analyzed so as to also yield other important physiologic variables, such as cardiac output and the central blood pressure waveform.

Exemplary embodiments of the present disclosure are described below. Further areas of applicability will become apparent from this description. The description is intended for the purposes of illustration and is not intended to limit the scope of the disclosure.

Figure 3:
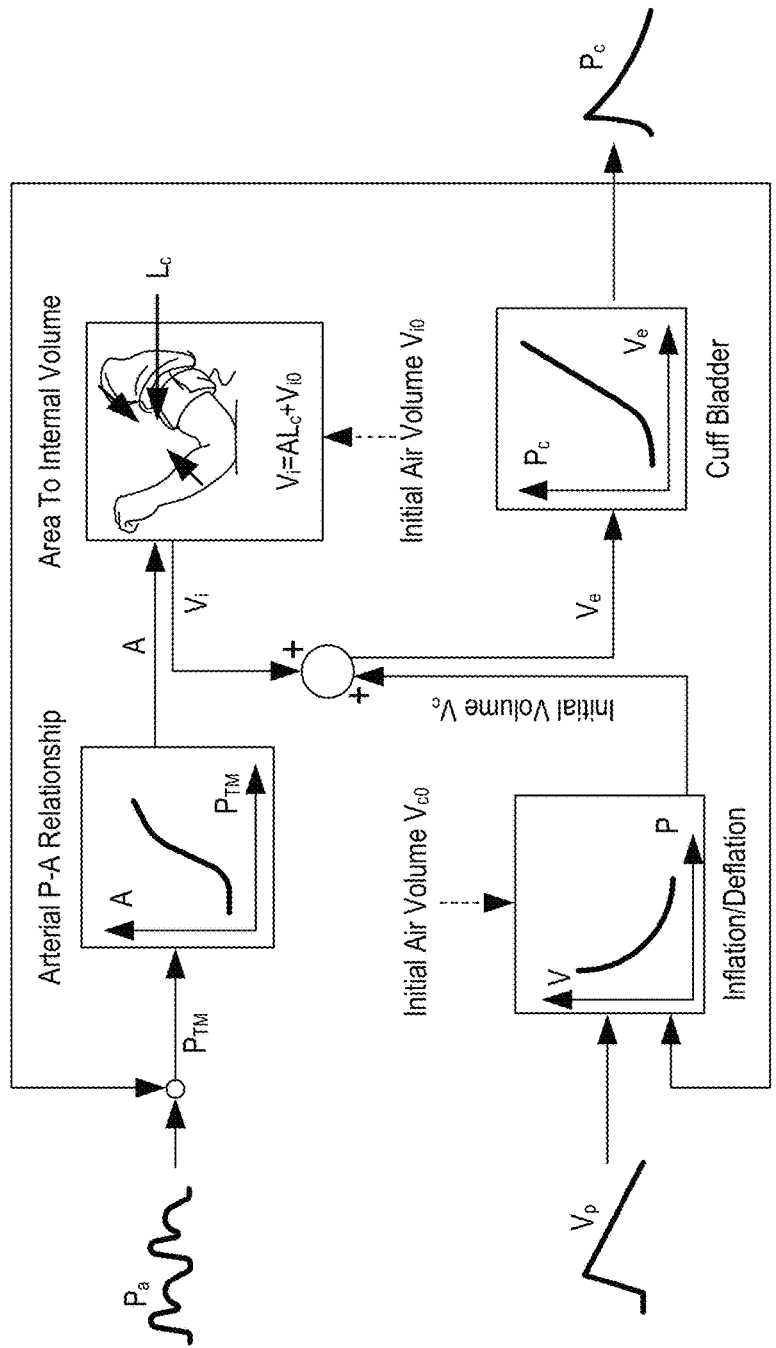
FIG. 3 is a diagram of a physical model of oscillometry.

Several physical models of oscillometry have been developed. For example, the model of Drzewiecki et al. (see Drzewiecki, G., R. Hood, and H. Apple. "Theory of the oscillometric maximum and the systolic and diastolic detection ratios". Ann Biomed Eng. 1994 January-February; 22(1):88-96) is illustrated in FIG. 3. This example model accounts for the pressure-dependent brachial artery compliance (Arterial P-A Relationship), the compressibility of air within the cuff as dictated by Boyle's law (Inflation/Deflation), and the deformation and stretch of the cuff bladder via a nonlinear pressure-volume relationship (Cuff Bladder). The arm tissue is assumed to be incompressible in this model. The inputs to the model are the brachial artery blood pressure waveform $P_a(t)$ and the volume of air pumped into and out of the cuff $V_p(t)$. The output is the cuff pressure $P_c(t)$, which also acts as feedback to both the blood vessel and the cuff. In this model, the cuff volume Mt is defined as the difference between the external sheath volume $V_e(t)$ and the inside volume contacting the arm ($V_i(t)$). Other types of physical models are also contemplated by this disclosure.

Arterial P-A Relationship: The cross-sectional area of the brachial artery A(t) is determined via its trans-mural pressure (i.e., the difference between blood pressure and cuff pressure ($P_{TM}(t)=P_a(t)-P_c(t)$)) according to the following nonlinear relationship:

$$A(t) = d \frac{\ln[aP_{TM}(t)+b]}{1+\exp[-cP_{TM}(t)]} \quad (1)$$

where a, b, c, and d are subject-specific parameters at the time of measurement. The brachial artery area A(t) is linked to the cuff through the volume of the arm $V_i(t)$ as follows:

$$V_i(t)=A(t)L_c+V_{i0} \quad (2)$$

where $L_c$ is the length of the arm cuff, and $V_{i0}$ is the initial arm volume for a collapsed brachial artery.

Cuff Bladder: The cuff pressure $P_c(t)$ is determined by the external cuff volume, which is the sum of the cuff volume and arm volume (i.e., $Mt)=Mt)+V_i(t)$), according to the following nonlinear relationship:

$$P_c(t)=E_c \cdot \{[V_e(t)/V_{e0}]^{1/n}-1\}^n \quad (3)$$

where $E_c$ is the maximum cuff elastance, $V_{e0}$ is the zero stretch volume of the bladder, and n is a constant of nonlinearity.

Inflation/Deflation: The cuff volume $V_c(t)$ is determined by the cuff pressure $P_c(t)$ and the volume of air pumped into and out of the cuff $V_p(t)$ according to Boyle's law as follows:

$$P_A[V_p+V_{c0}]=[P_A+P_c(t)]V_c(t) \quad (4)$$

where $P_A$ is atmospheric pressure, and $V_{c0}$ is the initial air volume in the cuff.

The two model inputs may be defined in terms of the following equations:

$$V_p(t) = \begin{cases} 81 \cdot t & 0 \le t \le 3 \\ 245 - 45 \cdot (t-3)/19 & t > 3 \end{cases} \quad (5)$$

and $$P_a(t) = \overline{P_a} + A_0 \sin\left(\frac{2\pi f_{HR}}{60}t + \phi_1\right) + A_1 \sin\left(\frac{4\pi f_{HR}}{60}t + \phi_2\right) \quad (6)$$

where $\overline{P_a}$ is MP, $f_{HR}$ is heart rate (HR) in Hz, and $A_0$, $A_1$, $\phi_1$, and $\phi_2$ are parameters defining PP and the waveform shape.

Some potentially useful alternatives include an Arterial P-A Relationship with fewer parameters or of a different form and a more accurate model of $P_a(t)$ (e.g., additional sinusoidal components). For a given $V_p(t)$ and $P_a(t)$ and set of model parameter values, the cuff pressure $P_c(t)$ may be computed by simultaneously solving the above equations for each time instant using a root-finding algorithm. In this way, the model is able to mimic the standard oscillometric cuff pressure waveform, which was its original purpose.

In one embodiment, a parametric physical model approach may be used to determine blood pressure. The main idea of this approach is to determine the unknown parameters of a physical model by fitting the model to the oscillometric cuff pressure waveform and to then compute the blood pressure values along with the entire blood pressure waveform using the determined parameters. For example, using the physical model of Drzewiecki et al., the following equation arises after combining Eqns. (1)-(4) and (6) and re-arranging terms:

$$A(t) = \frac{1}{L_c}\left\{V_{e0}\left[\left(\frac{P_c(t)}{E_c}\right)^{1/n}+1\right]^n - \frac{P_A}{P_A+P_c(t)}[V_p(t)+V_{c0}]-V_{i0}\right\} \quad (7)$$

$$= \frac{d \cdot \ln\left[a\left\{\overline{P_a}+A_0\sin\left(\frac{2\pi f_{HR}}{60}t+\phi_1\right)+A_1\sin\left(\frac{4\pi f_{HR}}{60}t+\phi_2\right)-P_c(t)\right\}+b\right]}{1+\exp\left[-c\left\{\overline{P_a}+A_0\sin\left(\frac{2\pi f_{HR}}{60}t+\phi_1\right)+A_1\sin\left(\frac{4\pi f_{HR}}{60}t+\phi_2\right)-P_c(t)\right\}\right]}$$

Here, $L_c$, $V_{e0}$, $E_c$, n, and $V_{c0}$ are determined from a priori experimentation on the employed cuff; $V_p(t)$ is the known volume of air pumped into and out of the cuff; $P_A$ is atmospheric pressure; $P_c(t)$ is measured via a sensor inside the cuff; $f_{HR}$ is measured from the oscillations in $P_c(t)$; and $\overline{P_a}$ is measured as the $P_c(t)$ at which the maximum amplitude oscillation occurs. Hence, all of these parameters or waveforms are known. But, the parameters a, b, c, d, $A_0$, $A_1$, $\phi_1$, and $\phi_2$ are patient and time specific and thus unknown. $\overline{P_a}$ may also be regarded as an unknown parameter. Further, the parameter a (and possibly other parameters) may be fixed to some value, as it has little impact on the Arterial P-A Relationship.

Alternatively, a PPG (e.g., placed on the finger) may be used to obtain a better approximation of $P_a(t)$ than Eqn. (6). For example, $P_a(t)$ may be approximated from the blood volume waveform measured with a PPG (u(t)) as follows:

$$P_a(t)=k_1 u(t)+k_2 \quad (8)$$

where $k_1$ and $k_2$ are unknown parameters. Substituting this equation into Eqn. (7) yields the following equation:

$$A(t) = \frac{1}{L_c}\left\{V_{e0}\left[\left(\frac{P_c(t)}{E_c}\right)^{1/n}+1\right]^n - \frac{P_A}{P_A+P_c(t)}[V_p(t)+V_{c0}]-V_{i0}\right\} \quad (9)$$

$$= \frac{d \cdot \ln[a\{k_1 u(t)+k_2-P_c(t)\}+b]}{1+\exp[-c\{k_1 u(t)+k_2-P_c(t)\}]}$$

The number of unknown parameters in this equation may be reduced by expressing $k_2$ in terms of $k_1$ using measured $\overline{P_a}$ as follows:

$$\overline{P_a} = k_1 \frac{\int_0^T u(\tau)d\tau}{T} + k_2 \Rightarrow k_2 = \overline{P_a} - k_1 \frac{\int_0^T u(\tau)d\tau}{T} \quad (10)$$

where T is the heart period. Note that another advantage of using a PPG is that the number of unknown parameters is reduced.

The unknown parameters are estimated by matching both sides of the second equality of Eqn. (7) or (9) to each other during some or all of the inflation/deflation period using a least squares search over a physiologic parameter range. Alternatively, a two-stage estimation approach may be used in which the numerator unknowns and denominator unknowns are identified in a sequential manner. Note that in the high trans-mural pressure regime, the denominator in the right-hand side of Eqn. (7) or (9) can be approximated as 1. So, first, the unknown parameters in the numerator are estimated by matching both sides of the equation during the high trans-mural pressure regime. Then, these estimated parameters are substituted in the equation, and the unknown parameters in the denominator are likewise estimated from the low trans-mural pressure regime. Other methods for estimating the parameters also fall within the broader aspects of this disclosure.

Finally, $P_a(t)$ is determined via Eqn. (6) or (8), and SP and DP are then given as the maximum and minimum of $P_a(t)$.

In another embodiment, a non-parametric physical model approach may be used to determine blood pressure. The main idea of this embodiment is to reduce the assumptions underlying the physical model by employing non-parametric models of the Arterial P-A Relationship and the blood pressure waveform and to then determine these non-parametric models from the oscillometric cuff pressure waveform. The trade-off in using non-parametric models instead of parametric ones includes reduced robustness to noise. For example, using the physical model of Drzewiecki et al., the following equation arises from the first equality in Eqn. (7):

$$A(t) = \frac{1}{L_c}\left(V_{e0}\left\{\left(\frac{P_c(t)}{E_c}\right)^{1/n} + 1\right\}^n - \frac{P_A}{P_A + P_C(t)}[V_p(t) + V_{c0}] - V_{i0}\right) \quad (11)$$

Figure 4A:
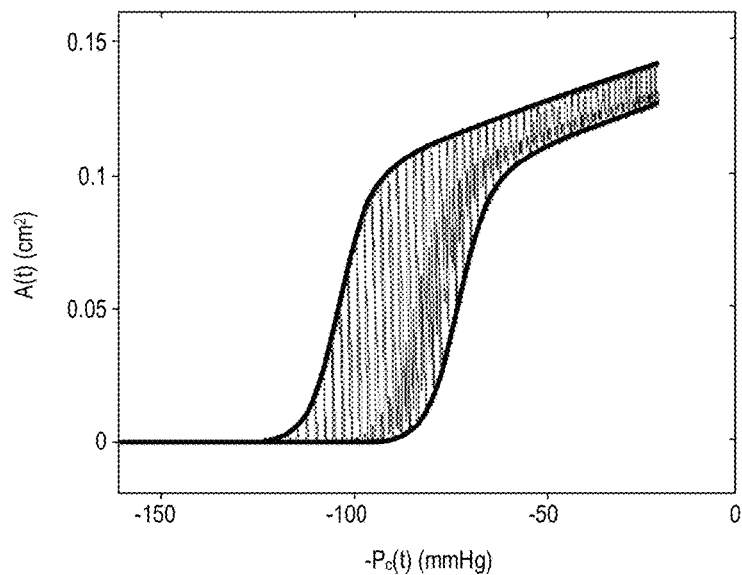
FIGS. 4A and 4B are graphs illustrating the determination of the Arterial P-A Relationship via a non-parametric method.
Figure 4B:
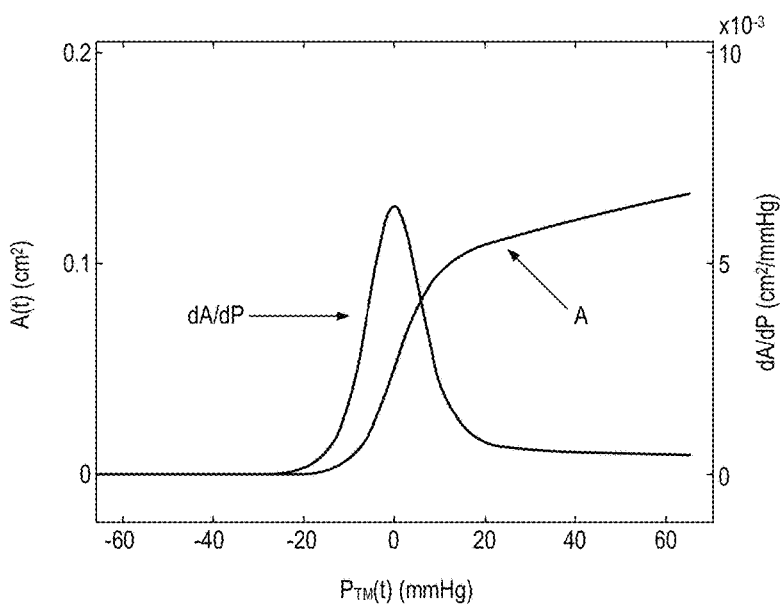
Figure 5A:
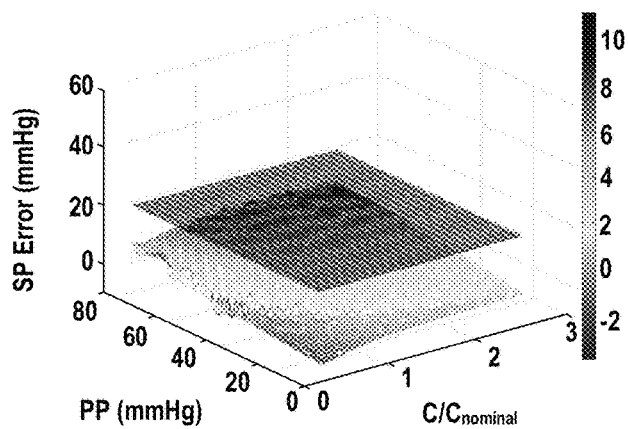
FIGS. 5A-5D are graphs depicting the performance of the non-parametric and fixed-ratio methods, respectively, on simulated oscillometric cuff pressure waveforms.
Figure 5B:
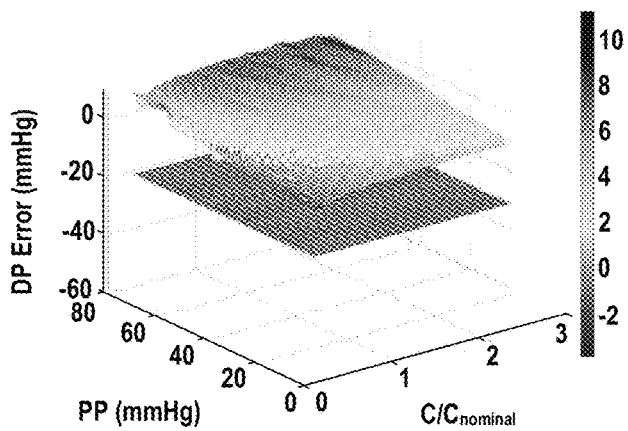
Figure 5C:
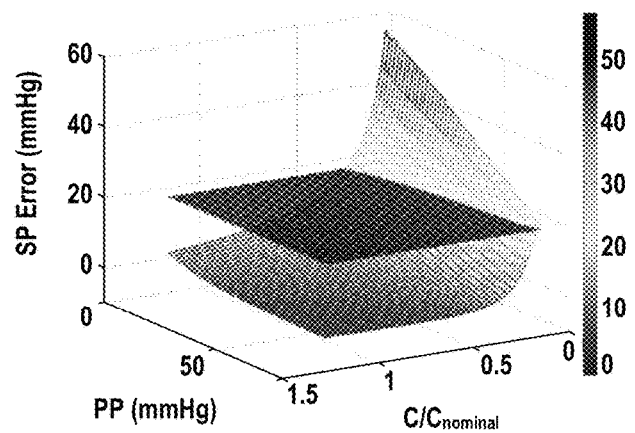
Figure 5D:
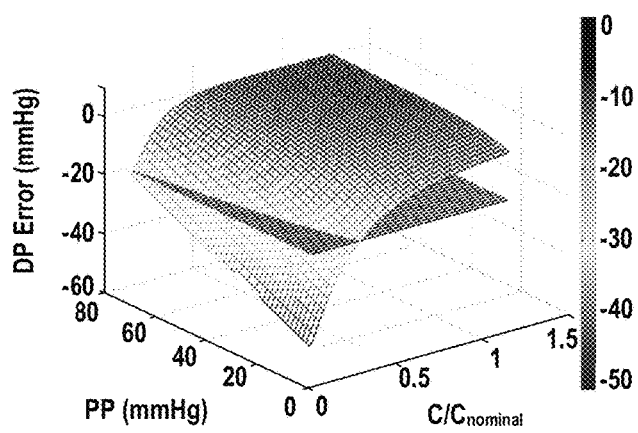

According to this equation, A(t) can be solved from the known cuff parameters and known $P_c(t)$ and $V_p(t)$ waveforms. Then, as shown in FIG. 4A, the upper or lower envelope (or some average of the two) of the plot relating A(t) to $-P_c(t)$ is identified to yield the Arterial P-A Relationship to within a horizontal offset equal to SP or DP (or some average of the two). Next, as indicated in FIG. 4B, the Arterial P-A Relationship is exactly determined by horizontally shifting it so that the peak derivative is located at zero trans-mural pressure. Thereafter, the resulting Arterial P-A Relationship is applied to compute $P_{TM}(t)$ from A(t). Finally, $P_c(t)$ is added to $P_{TM}(t)$ to yield $P_a(t)$. SP and DP are then determined as the maximum and minimum of this waveform. In this way, the Arterial P-A Relationship and $P_a(t)$ are obtained without assuming any model (e.g., Eqns. (1) and (6)).

A key assumption of the above embodiment is that the peak derivative of the Arterial P-A Relationship is located at zero trans-mural pressure. This assumption may not always be valid. For example, the assumption breaks down when the c parameter is very small, which corresponds to severe arterial stiffening in the neighborhood of zero trans-mural pressure. One potential solution is to vertically shift the computed $P_a(t)$ so that its mean value is equivalent to the $P_c(t)$ at which the maximum amplitude oscillation occurs.

Figure 6:
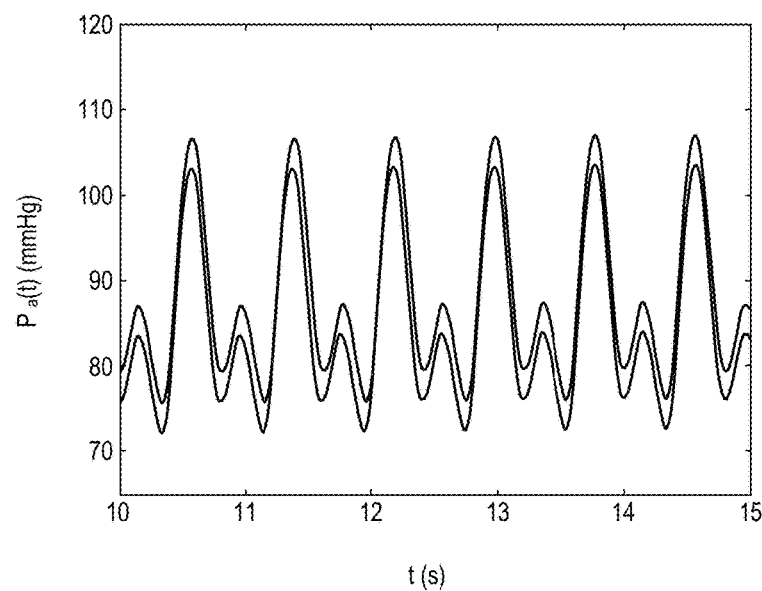
FIG. 6 is a graph illustrating an actual (simulated) blood pressure waveform and the waveform computed via the non-parametric method.

The non-parametric method described above (with the vertical shifting of $P_a(t)$) was tested using measurements simulated from the physical model of Drzewiecki et al. More specifically, $P_c(t)$ was simulated via Eqns. (1)-(6) using the nominal model parameter values given in Drzewiecki et al. The non-parametric method and the fixed-ratio method were applied to the simulated $P_c(t)$ to compute SP and DP, and the SP and DP errors were determined using the known values of SP and DP. This process was repeated for a range of values of PP and the c parameter. FIG. 5 shows that the non-parametric method was significantly more accurate than the fixed-ratio method, especially for low values of c (i.e., increased arterial stiffening in the zero-transmural pressure regime) and PP. FIG. 6 shows an example of the correspondence between the computed (red) and actual (blue) blood pressure waveforms.

As mentioned above, one drawback of the non-parametric method is that the peak derivative of the Arterial P-A Relationship does not always correspond to zero trans-mural pressure. While vertically shifting the resulting blood pressure waveform helps to mitigate this drawback, as shown in FIG. 5, it is an imperfect solution. Thus, a hybrid physical model approach forms the basis for yet another embodiment. The main idea of this embodiment is to combine components of the parametric and non-parametric approaches so as to eliminate the error introduced by the vertical shifting while preserving benefits of a non-parametric model and to then determine the hybrid model from the oscillometric cuff pressure waveform. For example, using the physical model of Drzewiecki et al., A(t) is solved from the known cuff parameters and known $P_c(t)$ and $V_p(t)$ according to Eqn. (11). Then, the Arterial P-A Relationship is obtained to within a horizontal offset as described above and shown in FIG. 4A. Next, this relationship is represented with the parametric model described above as follows:

$$A(t) = d\frac{\ln[a(SP - P_c(t)) + b]}{1 + \exp[-c(SP - P_c(t))]} \text{ for upper envelope} \quad (12)$$

$$A(t) = d\frac{\ln[a(DP - P_c(t)) + b]}{1 + \exp[-c(DP - P_c(t))]} \text{ for lower envelope} \quad (13)$$

Here, A(t) and $P_c(t)$ are known, while a, b, c, d, and SP and/or DP are unknown. These unknown parameters are determined by matching both sides of Eqn. (12) and/or (13) to each other during some or all of the inflation/deflation period using a least squares search over a physiologic parameter range or any other method known in the art. Finally, the resulting Arterial P-A relationship is applied to compute $P_a(t)$ from A(t) as described above.

The hybrid method described above was tested using measurements simulated from the physical model of Drzewiecki et al. The testing procedure was identical to that described above. This method was able to determine SP and DP and the blood pressure waveform without error.

Figure 7:
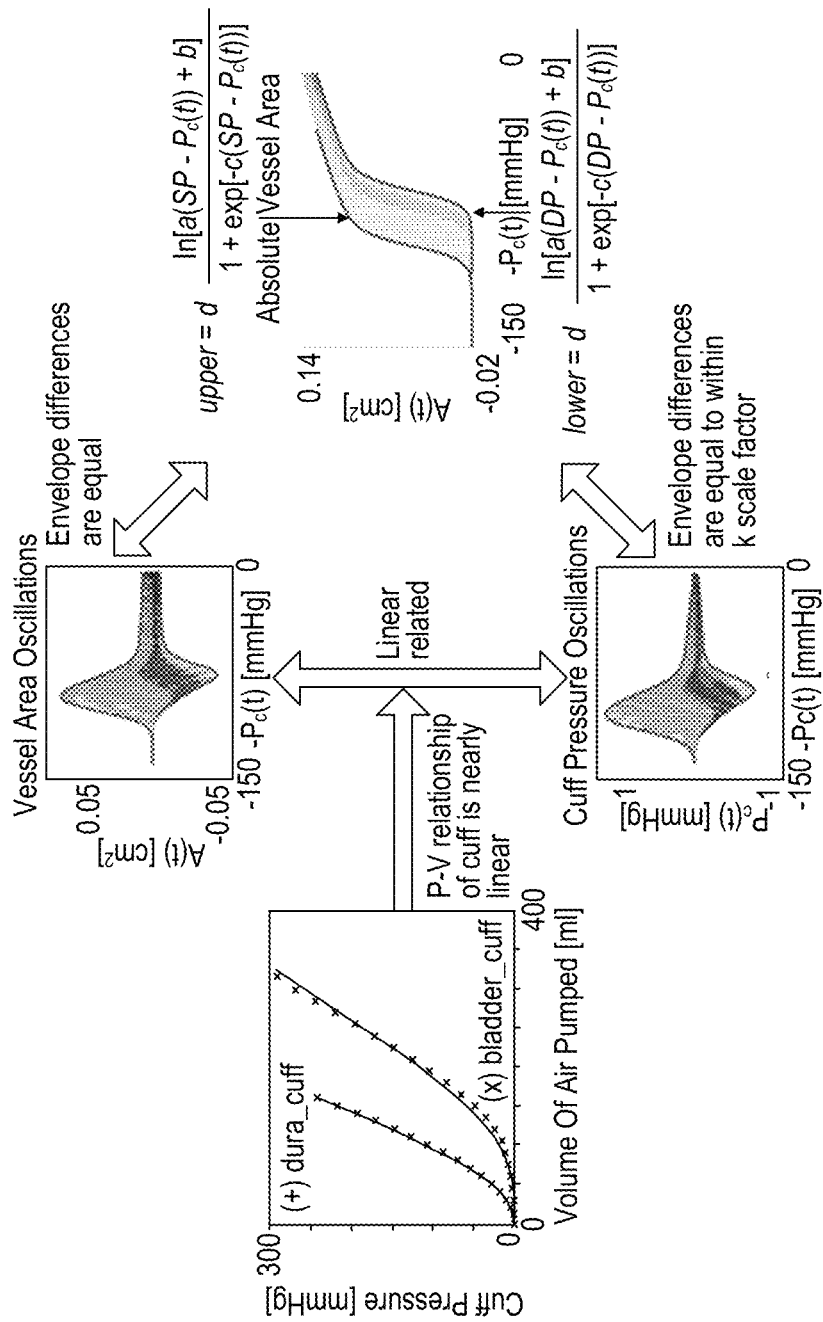
FIG. 7 is a diagram depicting the determination of blood pressure via a hybrid method without requiring detailed cuff information.
Figure 8A:
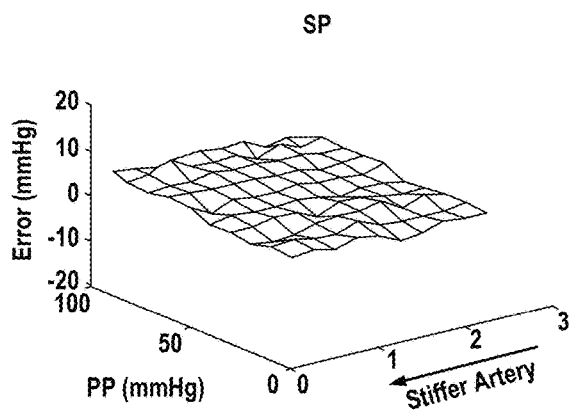
FIGS. 8A-8D are graphs depicting the performance of the second hybrid and fixed ratio methods on simulated oscillometric cuff pressure waveforms.
Figure 8B:
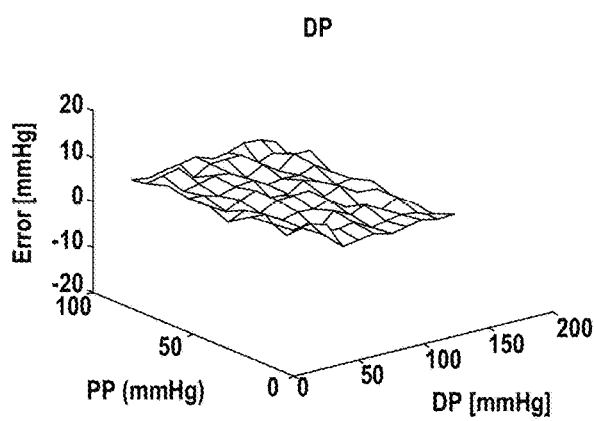
Figure 8C:
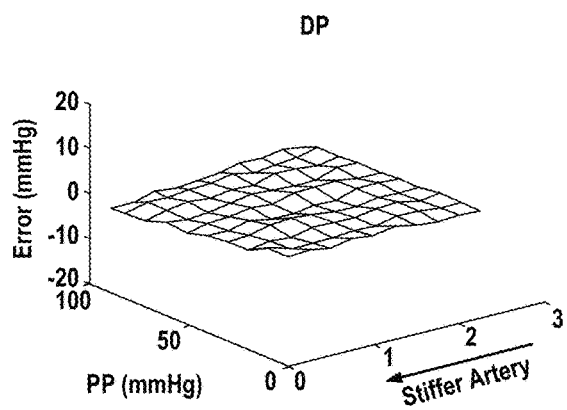
Figure 8D:
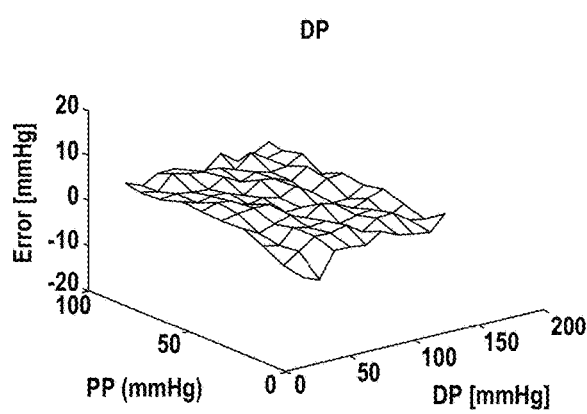

In a fourth embodiment, another hybrid physical model approach may be used to determine blood pressure. The main idea of this embodiment is similar to the original hybrid approach but is designed for the case in which the cuff parameters and volume of air pumped into and out of the cuff are unknown. For example, using the physical model of Drzewiecki et al., the original hybrid approach estimates blood pressure from A(t). However, calculation of A(t) requires detailed cuff information as indicated in Eqn. (11). To eliminate the need for this information, two observations are made. First, the difference in the upper and lower envelopes of the plot relating A(t) to $-P_c(t)$ is equal to the difference in the envelopes of the plot relating oscillations in A(t) to $-P_c(t)$ as shown in FIG. 7. Second, the pressure-volume relationship of the cuff is nearly linear over a wide range as also shown in FIG. 7. As a result, the measured and high-pass filtered $P_c(t)$ and the unmeasured oscillations in A(t) are assumed to be linearly related (e.g., y(t)=kx(t)+g). Note that this assumption becomes less tenable with decreasing blood pressure.

So, first, the difference in the upper and lower envelopes is detected from the plot relating the high-pass filtered $P_c(t)$ to $-P_c(t)$. Then, this envelope difference ($\delta P_c$) is represented as the difference in the parametric models for the Arterial P-A Relationships at systole and diastole as follows:

$$\delta P_c = e \frac{\ln[a(SP - P_c(t)) + b]}{1 + \exp[-c(SP - P_c(t))]} - e \frac{\ln[a(DP - P_c(t)) + b]}{1 + \exp[-c(DP - P_c(t))]} \quad (14)$$

Here, $\delta P_c$ and $P_c(t)$ are known, while a, b, c, e=kd, SP, and DP are unknown. These unknown parameters are determined by matching both sides of Eqn. (14) to each other during some or all of the inflation/deflation period using a least squares search over a physiologic parameter range or any other method known in the art. Finally, the resulting Arterial P-A Relationship to within a k scale factor is applied to the high-pass filtered $P_c(t)$ to compute $P_a(t)$.

Figure 9A:
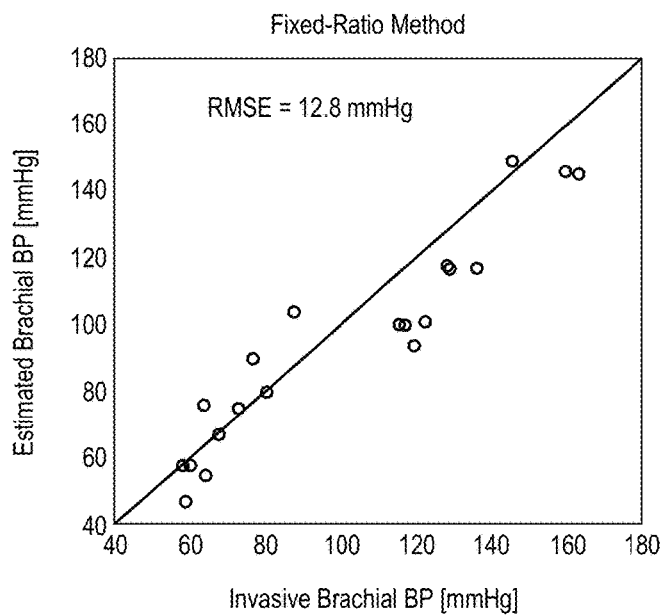
FIGS. 9A and 9B are graphs depicting the performance of the second hybrid method and the fixed-ratio-method on oscillometric cuff pressure waveforms from patients.
Figure 9B:
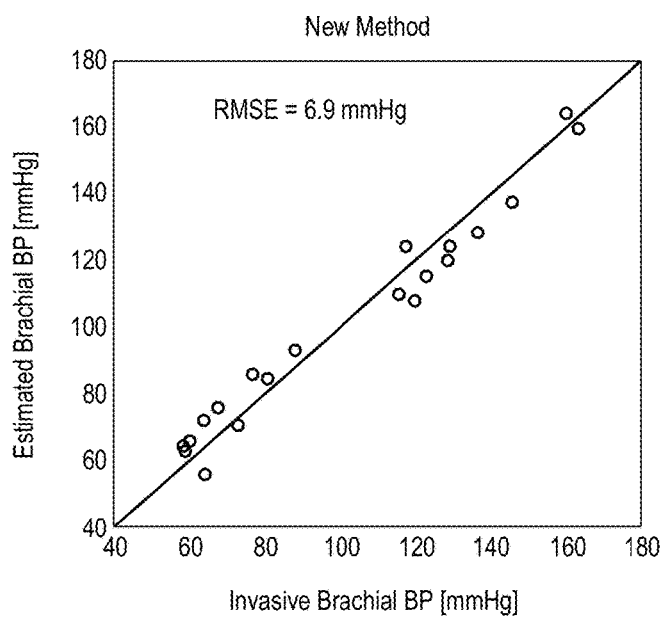

The second hybrid method described above was tested using measurements simulated from the physical model of Drzewiecki et al. The testing procedure was identical to that described above. FIG. 8 shows that this method was significantly more accurate than the fixed-ratio method even for a low DP range. The second hybrid method was also tested using measurements from 10 cardiology patients. For each patient, the oscillometric cuff pressure waveform via a standard arm cuff and reference blood pressure via an invasive brachial artery catheter were simultaneously measured. FIG. 9 shows that this method was more accurate than the fixed-ratio method (which was actually a commercial Omron system with a proprietary method for estimating DP and SP).

In a fifth embodiment, a physical model approach may be used to determine blood pressure from a finger-cuff PPG device. The idea of this embodiment is to measure the oscillometric blood volume waveform (which is proportional to A(t)) using the device rather than computing A(t) as done above. Then, the blood pressure waveform may be determined with either the parametric approach (e.g., via Eqn. (7) wherein the term following the first equality is ignored), non-parametric approach (e.g., as shown in FIG. 4), or the original hybrid approach (e.g., via Eqns. (12) and (13)) with the oscillometric blood volume waveform obtained with the PPG substituted for A(t). Note that the Arterial P-V (blood volume) relationship is also determined with any of these methods. Hence, the blood pressure waveform may be subsequently measured using this relationship without any cuff inflations and deflations. More specifically, the cuff pressure is held constant, and the waveform obtained from the PPG is mapped through the relationship to determine $P_{TM}(t)$. Then, the constant cuff pressure is added to this waveform to arrive at $P_a(t)$. A lower constant cuff pressure will be more tolerable to the subject, while a constant cuff pressure near MP may be more accurate. Hence, a constant cuff pressure that is sub-DP may represent a good compromise. Since the Arterial P-V relationship can change (e.g., with vasomotor tone), it should be periodically computed (e.g., every 5 to 15 min) via cuff inflation and deflation to yield the oscillometric blood volume waveform. In addition, if the subsequent MP is very different from the MP determined from cuff inflation and deflation, then the Arterial P-V relationship could be re-computed. In this way, the blood pressure waveform may be continuously obtained from a finger-cuff PPG device without invoking the arterial unloading principle.

The techniques described herein may be implemented by one or more computer programs executed by one or more processors. The computer programs include processor-executable instructions that are stored on a non-transitory tangible computer readable medium. The computer programs may also include stored data. Non-limiting examples of the non-transitory tangible computer readable medium are nonvolatile memory, magnetic storage, and optical storage.

Some portions of the above description present the techniques described herein in terms of algorithms and symbolic representations of operations on information. These algorithmic descriptions and representations are the means used by those skilled in the data processing arts to most effectively convey the substance of their work to others skilled in the art. These operations, while described functionally or logically, are understood to be implemented by computer programs. Furthermore, it has also proven convenient at times to refer to these arrangements of operations as modules or by functional names, without loss of generality.

Unless specifically stated otherwise as apparent from the above discussion, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system memories or registers or other such information storage, transmission or display devices.

Certain aspects of the described techniques include process steps and instructions described herein in the form of an algorithm. It should be noted that the described process steps and instructions could be embodied in software, firmware or hardware, and when embodied in software, could be downloaded to reside on and be operated from different platforms used by real time network operating systems.

Figure 10:
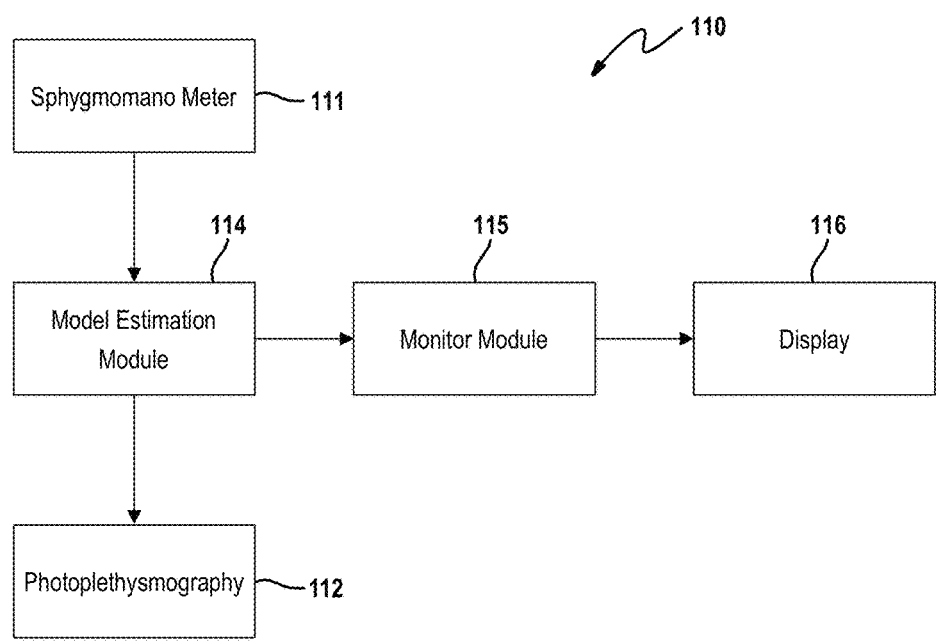
FIG. 10 is a diagram of an example system that implements methods for determining cuff blood pressure.

FIG. 10 depicts an example system 110 that implements one or more of the methods described above. The system 50 is comprised generally of a sphygmomanometer 111, a model estimation module 114, a monitor module 116 and at least one output device, such as display 116. The system may also include a photoplethysmograph 112. It can be appreciated that other types of sensors may also be part of the system.

The sphygmomanometer 111 is configured to measure blood pressure of a subject. The sphygmomanometer 111 includes a cuff and a pressure sensor integrated therein as is readily understood in the art. It is envisioned that the method described above may be implemented using similar types of pressure meters.

In operation, the model estimation module 114 is configured to receive an oscillometric cuff pressure waveform from the sphygmomanometer 111. The model estimation module 114 is also configured to receive a measure of the volume of air pumped into and out of the cuff. From these and other inputs, the model estimation model 114 can determine parameters of a physical model that accounts for mechanics of the cuff, an artery and coupling between the cuff and the artery. The parameters of the model can be determined by implementing the various methods described above. In an exemplary embodiment, the model is preconfigured in a data store of the system and thus accessible to the parameter determination module 54.

Given the determined parameter values of the model, the monitor module 116 can compute the blood pressure waveform of the subject. In this way, the estimation of blood pressure is specific to the subject at the time of measurement and therefore more accurate. In some embodiments, the model estimation module 114 may also receive a blood volume waveform, for example using a finger-cuff photoplethysmography. The monitor module 116 can in turn determine the blood pressure waveform based in part on the measured blood volume waveform.

In some embodiments, the monitor module 116 may monitor computed blood pressure and trigger alarms when monitored quantities exceed thresholds. In other embodiments, the monitor module 116 may administer therapy to the subject or modify the subject's therapy, based on the monitored blood pressure. Lastly, the monitor module 116 may interface with the display 118 to present the monitored blood pressure on the display 118. However, it can be appreciated that other types of output devices may be used in lieu of the display device.

This system 110 may be specially constructed for the required purposes, or it may comprise a general-purpose computer selectively activated or reconfigured by a computer program stored on a computer readable medium that can be accessed by the computer. Such a computer program may be stored in a tangible computer readable storage medium, such as, but not limited to, any type of disk including floppy disks, optical disks, CD-ROMs, magnetic-optical disks, read-only memories (ROMs), random access memories (RAMs), EPROMs, EEPROMs, magnetic or optical cards, application specific integrated circuits (ASICs), or any type of media suitable for storing electronic instructions, and each coupled to a computer system bus. Furthermore, the computers referred to in the specification may include a single processor or may be architectures employing multiple processor designs for increased computing capability. In other embodiments, the term module can refer to an application specific integrated circuit (ASIC), an electronic circuit, a combinational logic circuit, and/or other suitable components that provide the described functionality.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A method for determining blood pressure for a subject using a sphygmomanometer having a cuff and a pressure sensor integrated therein, comprising:
    measuring an oscillometric cuff pressure waveform of the subject using the sphygmomanometer, where the oscillometric cuff pressure waveform indicates the time evolution of the pressure inside the cuff during inflation and deflation of the cuff;
    measuring volume of air pumped into and out of the cuff during inflation and deflation of the cuff;
    determining the cross-sectional area waveform of the artery underneath the cuff using the volume of air pumped into and out of the cuff and the measured oscillometric cuff pressure waveform;
    determining an envelope of the cross-sectional area waveform as a function of the measured oscillometric cuff pressure waveform; and
    determining, by the computer processor, blood pressure for the subject using the envelope.

2. A method for determining blood pressure for a subject using an oscillometric cuff device, comprising:
    measuring cuff pressure using an oscillometric cuff device by inflating and deflating a cuff placed over an artery of the subject;
    deriving an oscillogram from the measured cuff pressure, where the oscillogram is an amplitude of oscillations in the measured cuff pressure as a function of the measured cuff pressure;
    determining an envelope difference between an upper envelope of the oscillogram and a lower envelope of the oscillogram;
    representing the envelope difference as a difference in a parametric model, where the parametric model is defined in terms of parameters with unknown values and specifies a nonlinear area-pressure relationship of the artery underneath a cuff of the oscillometric cuff device at systole and diastole;
    estimating values for all of the parameters of the parametric model simultaneously by fitting the parametric model to the envelope difference including amplitude of the envelope difference; and
    determining blood pressure from the subject from the values of the parameters of the parametric model.

3. The method of claim 1 wherein determining the cross-sectional area waveform of the artery further comprises determining an absolute cross-sectional area waveform using known parameters for the cuff of the sphygmomanometer, the volume of air pumped into and out of the cuff physical model and the measured oscillometric cuff pressure waveform.

4. The method of claim 1 wherein determining blood pressure for the subject using the envelope further comprises representing the envelope with a physical model with unknown parameters and fitting the physical model to the envelope to estimate the parameters, where blood pressure is one of the estimated parameters of the physical model.

5. The method of claim 1 wherein determining blood pressure for the subject using the envelope further comprises horizontally shifting the envelope to yield an arterial area-pressure relationship, applying the cross-sectional area waveform to the arterial area-pressure relationship to yield transmural pressure, and then adding cuff pressure to the transmural pressure to yield blood pressure.

6. A method for determining blood pressure for a subject using an oscillometric cuff device, comprising:

measuring cuff pressure using an oscillometric cuff device by inflating and deflating a cuff placed over an artery of the subject;

deriving an oscillogram from the measured cuff pressure, where the oscillogram is an amplitude of oscillations in the measured cuff pressure as a function of the measured cuff pressure;

determining an envelope difference between an upper envelope of the oscillogram and a lower envelope of the oscillogram;

representing the envelope difference as a difference in a parametric model, where the parametric model is defined in terms of parameters with unknown values and specifies a nonlinear area-pressure relationship of the artery underneath a cuff of the oscillometric cuff device at systole and diastole;

estimating values for the parameters of the parametric model by fitting the parametric model to a portion of the envelope difference; and determining blood pressure from the subject from the values of the parameters of the parametric model.

\* \* \* \* \*